United States Patent [19]

Leach et al.

[11] 4,108,909

[45] Aug. 22, 1978

[54] N-ALKYLATED CRESYLIC ACIDS VIA DIRECT ALKYLATION IN A LIQUID PHASE

[75] Inventors: Bruce Eugene Leach; Charles M. Starks, both of Ponca City, Okla.

[73] Assignee: Continental Oil Company, Ponca City, Okla.

[21] Appl. No.: 742,931

[22] Filed: Nov. 18, 1976

Related U.S. Application Data

[63] Continuation-in-part of Ser. No. 650,225, Jan. 19, 1976, abandoned.

[51] Int. Cl.$^2$ .................. C07C 39/08; C07C 39/06
[52] U.S. Cl. .................................... 568/766; 568/794
[58] Field of Search .............. 260/624 C, 626 R, 625, 260/624 R

[56] References Cited

U.S. PATENT DOCUMENTS

| | | | |
|---|---|---|---|
| 2,448,942 | 9/1948 | Winkler et al. | 260/621 R |
| 3,426,358 | 2/1969 | Schlichting | 260/621 R |
| 3,843,606 | 3/1975 | Van Sorge | 260/621 R |
| 3,974,229 | 8/1976 | Van Sorge | 260/624 C |

Primary Examiner—James O. Thomas, Jr.
Assistant Examiner—W. B. Lone
Attorney, Agent, or Firm—Cortlan R. Schupbach, Jr.

[57] ABSTRACT

A method for the production of n-alkylated cresylic acids such as n-hexyl resorcinol by direct alkylation of a cresylic acid such as resorcinol under liquid phase conditions.

7 Claims, No Drawings

N-ALKYLATED CRESYLIC ACIDS VIA DIRECT ALKYLATION IN A LIQUID PHASE

This is a continuation in part of U.S. Ser. No. 650,225, filed Jan. 19, 1976 and now abandoned.

This invention relates to the liquid phase alkylation to produce n-alkylated cresylic acids by contacting a cresylic acid with an alcohol or ethylene. More specifically, this invention relates to a method for the production of n-hexyl resorcinol by direct alkylation of resorcinol under liquid phase conditions.

Many commercial applications exist for n-alkylated cresylics. For example, 4-n-hexyl resorcinol is an antiseptic and an anthelmintic. This particular compound is commonly prepared by condensing hexanoic acid with resorcinol and reducing the resulting ketone using a mercury-zinc amalgam. The prior art reaction is shown in Equation I.

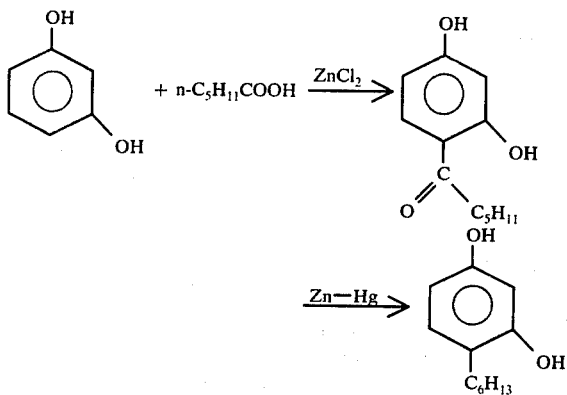

The condensation step encountered in the prior art is not exceedingly difficult, although a glass-lined reactor is normally required because of the zinc chloride involved. The zinc chloride can be regenerated and reused. The main problem with the prior art procedure arises from the reduction using a zinc-mercury amalgam because of mercury contamination problems. These contamination problems, combined with the exceedingly high cost of the zinc-mercury amalgam, contribute to the high cost of this 4-hexyl resorcinol.

It would therefore be distinctly advantageous to provide a process for the production of compounds such as n-hexyl resorcinol using a method which does not involve the expensive zinc-mercury amalgam with its attendant contamination problems nor the condensation in the presence of toxic zinc chloride, requiring glass-lined reactors and recovery of materials, and to produce primarily an n-alkylated side chain. Previous attempts to directly alkylate resorcinol such as described in U.S. Pat. No. 2,448,942, produced not n-hexyl resorcinol, but isohexyl resorcinol, which does not have the properties necessary to act as an antiseptic and anthelmintic in humans.

It is therefore an object of the present invention to provide a method for the direct alkylation of a cresylic acid with an aliphatic compound to produce cresylic acids having predominately n-alkylated side chains. Other objects will become apparent to those skilled in this art as the description proceeds.

It has now been discovered according to the present invention that n-alkylated cresylic acids can be prepared by contacting a cresylic acid with an aliphatic compound selected from the group consisting of n-alcohols and carrying out a direct alkylation utilizing pressures of from about atmospheric pressure to about 1,000 pounds per square inch gauge (psig) and temperatures of from about 200° C to 400° C in the presence of aluminum oxide and from 300° C to 500° C in the presence of magnesium oxide catalysts. In some reactions, the presence of water is found to be helpful. If water is not present, reaction temperatures are normally from about 330° C to 340° C. Normally, from about .1 to about 1 mole of water per mole of cresylic acid will be used. However, from about 0.4 to about 0.6 mole is preferred.

Representative examples of alcohols useful in the practice of the present invention are n-alcohols containing from 4 to 10 carbon atoms. Representative examples of such alkanols are n-butanol, n-pentanol, n-hexanol, n-heptanol, n-octanol, n-nonanol, and n-decanol.

Ethylene is also useful in the practice of the present invention to provide an aliphatic moiety. Higher alkenes tend to form isomerized products rather than n-alkylated compounds.

Cresylic acids useful in the practice of the present invention are phenol and mixtures of phenols. Representative examples of such compounds are phenol, o-cresol, p-cresol, m-cresol, isomeric xylenols, hydroquinone, and resorcinol.

The most preferred compound produced by the practice of the present invention is n-hexyl resorcinol because of its large commercial market and antiseptic properties. However, it should be understood that the process of the present invention is effective to prepare other n-alkylated cresylic acids as well. The process of the present invention allows direct alkylation of the cresylic rings without excessive isomerization of the alkyl moiety.

Representative examples of catalysts useful in the present invention are alumina catalysts and magnesium oxides. While all alumina catalysts will be effective, it has been found that aluminas prepared as a by-product of an aluminum alkyl hydrolysis are most effective. Representative examples of such aluminas are CATAPAL and DISPAL aluminas, trademarks of and sold by Continental Oil Company. When these preferred aluminas are used as catalysts, lower pressures and temperatures can be used than when aluminas from other sources or magnesium oxide is used. Normally these preferred aluminas allow reactions to occur at temperatures of from about 230° to about 300° C and pressures of 1–20 atmospheres together with continuous removal of water. These decreased temperatures and pressures allow still less isomerization of side chains than found with alumina catalysts generally and magnesium oxide catalysts, although even these, under the conditions set forth, are a great improvement over the prior art processes where primarily side-chain isomerization was found.

Although the reaction can be carried out either batchwise of continuously, continuous reactions are preferred. When carried out continuously, liquid hourly space velocities of from about 0.01 to about 30, but from about 0.1 to 3 is preferred.

The invention is more concretely described with reference to the example below wherein all parts and percentages are by weight unless otherwise specified. The examples should be construed to exemplify the present invention and in no way limit it.

EXAMPLE 1

An electrically heated ½-inch diameter stainless steel tube containing 15 milliliters of CATAPAL SB alumina extrudate was used as a reactor. All reactants were pumped through a preheater into the reactor and were cooled before exiting through a back pressure regulator maintaining a system pressure of 300 pounds per square inch gauge. The feed composition was 1 mole of resorcinol (110.1 grams), 0.4 mole of n-hexanol (40.8 grams), and 0.5 mole of water (9.0 grams). A reaction temperature of between 340° and 360° C was investigated. Conversion increased with temperature, and selectivity to the desired products remained nearly constant. The major products were n-hexyl resorcinol, the n-hexyl ether of resorcinol, and isohexyl resorcinol. The ether was recycled. The ratio of normal to isohexyl resorcinol product was 70 to 30, respectively.

EXAMPLE 2

A mixture of 55 grams (0.5 mole) resorcinol and 51 grams (0.5 mole) of 1-hexanol is heated until a liquid state is obtained and pumped continuously into a reactor containing 128 milliliters (ml) of a high surface area magnesium oxide catalyst, such as Mg-0601T, sold by Harshaw Chemical Company. Such catalysts are normally in the form of pellets. The reactor is maintained at a temperature of from about 500°–505° C and a pressure of about 300 psig during the course of the reaction. Analysis of the product shows the presence of 4-n-hexyl resorcinol.

EXAMPLE 3

A reaction is carried out as described in Example 1 except that water is excluded from the feed composition. At the temperature used, the product composition and distribution is nearly the same even in the absence of water.

The following examples illustrate the effectiveness of aluminas derived from aluminum alkoxide hydrolysis. Aluminas used were CATAPAL® SB alumina, except for Example 9, which used ALCOA F1 Alumina and is inserted for comparative purposes.

EXAMPLE 4

In a 500 ml flask fitted with thermometer, mechanical stirrer, addition funnel, and a Dean-Stark trap, with attached condenser is placed 110g of resorcinol and 71.4g of 1-hexanol. The reaction mixture was heated at 160°–200° C for 4 hours with no apparent reaction taking place. Alumina (15g) was added and the mixture heated gradually to 255° C over a period of 4 hours, 1.8 ml of water having been produced. Hexanol was removed from the reaction by drawing off through the Dean-Stark trap to allow the temperature to reach 255° C. Refluxing was continued at 240°–255° C with the reflux temperature being controlled by the periodic addition of hexanol (that which had been removed) back to the reaction mixture. This procedure was continued over a period of about 8 hours, during which time all of the original hexanol had been added back to the reaction mixture, and during which 16.7 ml of produced water had been collected in the Dean-Stark trap. The reaction mixture was analyzed at this point (using o-cresol as an external standard) and was found to have the following composition, as determined by area under a gas chromatograph curve.

|  | Area % |
|---|---|
| Hexenes | 2.25 |
| 1-hexanol | 7.31 |
| Resorcinol | 16.23 |
| Monohexylether of Resorcinol | 3.37 |
| 2-n-hexylresorcinol | 1.93 |
| 4-n-hexylresorcinol | 18.93 |
| Sec-hexylresorcinol | 1.82 |
| Dihexylresorcinols | 8.89 |
| Non-Eluting Material | 39.27 |

A part of the crude reaction product (ca 90g was taken up in 500 ml of diisopropyl ether and washed with one 300 ml portion of 1N sulfuric acid and then with five 300 ml portions of water. The combined aqueous phases were back-extracted with 100 ml of diisopropyl ether, and this was combined with the other organic phase. Isopropyl ether was mostly removed from the organic material on a rotary evaporator. The residue 142.g was charged to a 4-foot spinning band fractional distillation column and distilled, the results shown in Table 1.

Table 1

| Cut No. | b.p. | wt. g |
|---|---|---|
| 1 | 50–71° 1 atm. | 67.0g |
| 2 | 48–138 at 2 torr | 9.6g |
| 3 | 142–162 at 2 torr | 9.1g |
| 4 | 174–176 at 2 torr | 20.2g |
| 5 | 176–219 at 2 torr | 8.3g |
| Residue | — | 17.4g |
| Trap | — | 2.0g |
| Loss and Hold-up | — | 8.8g |

The individual cuts were analyzed by gas chromatography. Cut 1 was essentially pure diisopropyl ether with about 8 percent hexenes. The compositions of the other cuts are listed in Table 2.

Table 2
ANALYSIS OF DISTILLATION CUTS

| Component | Area % of Cut | | | | Total wt, Grams |
|---|---|---|---|---|---|
|  | 2 | 3 | 4 | 5 |  |
| Hexanol | 53.92 | 0.52 | — | — | 5.22 |
| Resorcinol | 31.62 | 38.98 | 0.52 | — | 6.58 |
| Mono-n-hexylether of resorcinol | 3.10 | 24.70 | 2.58 | 0.99 | 3.15 |
| 2-n-hexylresorcinol | 0.11 | 7.05 | 4.05 | 1.18 | 1.56 |
| 4-n-hexylresorcinol | 0.10 | 3.47 | 84.62 | 14.17 | 18.60 |
| Sec-hexylresorcinols | — | 0.54 | 5.47 | 10.61 | 2.03 |
| Dihexylresorcinols | — | — | 2.10 | 64.00 | 5.73 |
| Others | 11.15 | 24.74 | 0.66 | 9.05 | — |

The isolated yield of 4-n-hexylresorcinol amounts to about 24 wt %.

A portion of cut 4, 5g. was recrystallized from petroleum ether to yield light yellow platelets, m.p. 57° C (m.p. of 4-n-hexylresorcinol is 61° C). The proton magnetic resonance spectrum of the recrystallized material was identical with that of a known sample of 4-n-hexylresorcinol.

EXAMPLE 5

The reaction of 1-hexanol with resorcinol over alumina was repeated, except that samples of the reaction mixture were removed at various conversion levels and analyzed. Thus, to a mixture of 110g (1.0 mole) of resorcinol and 20g of calcined powdered CATAPAL® SB alumina, heated to 255° C, was added 102g (1.0 mole) of 1-hexanol at such a rate as to maintain the temperature at 250°–260° C (about 8–10 hours) with vigorous reflux. Samples of the reaction mixture were removed as follows:

| Reaction Time Hours | ml of Water Produced | Sample No. |
| --- | --- | --- |
| 3 | 7 | 1 |
| 5 | 10 | 2 |
| 7 | 14 | 3 |
| 10 | 18 | 4 |
| 14 | 22 | 5 |

These samples were weighed into a weighed amount of m-cresol (used as an external gas chromatography standard) and analyzed on a 10 foot × ⅛ inch SE-30 gas chromatography column programmed from 100° to 350° C at 10° per minute. Results of these analyses are listed in Table 3.

Table 3
ANALYSIS OF SAMPLES FROM EXAMPLE 5

| Component | PERCENT, IN SAMPLE NO. | | | | |
| --- | --- | --- | --- | --- | --- |
| | 1 | 2 | 3 | 4 | 5 |
| 1-Hexanol | 14.48 | 6.44 | 6.42 | 12.97 | 3.57 |
| Resorcinol | 46.77 | 28.03 | 19.40 | 9.68 | 4.83 |
| Light Unknowns | 2.57 | 2.67 | 2.12 | 2.42 | 1.13 |
| Hexyl Resorcyl Ether | 4.66 | 4.12 | 4.19 | 3.46 | 3.31 |
| 2-n-hexylresorcinol | 1.63 | 1.59 | 2.04 | 1.64 | 2.82 |
| 4-n-hexylresorcinol | 9.61 | 16.87 | 20.74 | 18.81 | 15.86 |
| Sec-hexylresirconols | 3.26 | 0.76 | 3.18 | * | 1.71 |
| Di- & trihexylresorcinols | 4.23 | 5.80 | 12.21 | * | * |
| Non-Eluting Material | 12.79 | 33.72 | 29.70 | 51.02 | 66.77 |

*These components were not well analyzed. They are lumped into the non-eluting material figure.

The data of Table 3 allows conversions and selectivities to be calculated, where weight percent selectivity is defined as the percent of 4-n-hexylresorcinol × 100/wt % of all components except water, unreacted hexanol, unreacted resorcinol, and hexyl resorcyl ether.

| | SAMPLE NO. | | | | |
| --- | --- | --- | --- | --- | --- |
| | 1 | 2 | 3 | 4 | 5 |
| Approximate Wt % Conversion of Resorcinol | 42.6 | 57.8 | 66.9 | 81.5 | 90.8 |
| Wt % Selectivity to 4-n-Hexylresorcinol | 14.6 | 27.5 | 29.6 | 25.5 | 18.0 |

EXAMPLE 6

The reaction of example 4 is repeated, except that it is conducted in an autoclave wherein the pressure may be maintained at 75 psig. 1-hexanol is fed into the reactor by a pump, which, in turn, is controlled by a temperature actuated switch, so that as the temperature reaches 250° C, hexanol is pumped in until the reflux temperature drops to just below 250° C. As the hexanol is consumed, and the water removed via the trap, the temperature rises to just above 250° C whereupon the pump is again actuated and more hexanol added. In this way, the steady-state concentration of hexanol in the reaction mixture is increased.

EXAMPLE 7

4-n-octyl resorcinol is prepared by heating 1-octanol with resorcinol in the presence of 20 wt % alumina. The 1-octanol is added at such a rate that the temperature is maintained at 275° C, with continuous removal of the water formed.

EXAMPLE 8

3-ethyl-1-pentanol (81g, 0.6 mole) is added to resorcinol (110g, 1.0 mole) and 50g of activated alumina at such a rate as to maintain the temperature at 240°–250° C, with continuous removal of the water that is formed. 4-(3-ethyl-1-pentyl) resorcinol is formed.

Example 9 is a comparative example using aluminas derived from sodium aluminate. When compared to Example 4 results, the selectivity of aluminas derived from aluminum alkoxide hydrolysis is clearly seen.

EXAMPLE 9

The reaction of 1-hexanol and resorcinol, as conducted in Example 4, was repeated except that the alumina used was ALCOA F1 alumina, rather than CATAPAL® alumina. No 4-n-hexylresorcinol production was observed.

It will be apparent from the process described herein that a much improved process is provided for the preparation of n-alkylated cresylic acids. The use of toxic, expensive, and corrosive materials such as zinc chloride for condensation is avoided as is the use of an expensive and polluting zinc-mercury amalgam. The process of the instant invention consists of but a single step and can be carried out in a continuous reactor to produce a mixture containing the products desired.

While certain embodiments and details have been shown for the purpose of illustrating this invention, it will be apparent to those skilled in this art that various changes and modifications may be made herein without departing from the spirit or the scope of the invention.

We claim:

1. A method for the production of a phenolic compound containing predominantly n-alkylated side chains by contacting a compound selected from the group consisting of resorcinol, phenol, isomerized xylenols, hydroquinone, o-cresol, p-cresol and m-cresol with an n-alkanol having from 4 to 10 carbon atoms and wherein direct alkylation is carried out at pressures of from about 1 atmosphere to about 20 atmospheres, temperatures of from about 200° C to about 400° C in the presence of an alumina catalyst derived from aluminum alkoxide hydrolysis.

2. A method as described in claim 1 wherein in addition the reaction mixture contains water at a level of from about .1 mole to about 1 mole based upon the amount of phenolic compound.

3. A method as described in claim 2 wherein the reaction is carried out in a continuous reactor.

4. A method as described in claim 2 wherein the alkylating compound is an n-alcohol selected from the group consisting of n-hexanol, n-pentanol, n-butanol, n-octanol, n-heptanol, n-nonanol, and n-decanol.

5. A method as described in claim 1 wherein the phenolic compound is resorcinol, the alkylating compound is n-hexanol, the catalyst is an alumina catalyst derived from aluminum alkoxide hydrolysis, and the reaction is carried out at temperatures of from about 230° C to about 300° C.

6. A method for the production of a phenolic compound containing predominately n-alkylated side chains by contacting a compound selected from the group consisting of resorcinol, phenol, isomerized xylenols, hydroquinone, o-cresol, p-cresol and m-cresol with an n-alkanol having from 4 to 10 carbon atoms and wherein direct alkylation is carried out at pressures of from about -1- to about 20 atmospheres, temperatures of from about 230° C to about 300° C in the presence of an alumina catalyst derived from aluminum alkoxide hydrolysis, and wherein water is continuously removed from the reaction as formed.

7. A method as described in claim 6 wherein the n-alkanols are selected from the group consisting of n-hexanol, n-pentanol, n-butanol, n-octanol, n-heptanol, n-nonanol, and n-decanol.

* * * * *